(12) United States Patent
Bui

(10) Patent No.: US 10,905,839 B1
(45) Date of Patent: Feb. 2, 2021

(54) PATIENT AIRWAY DOME AND METHODS OF MAKING AND USING SAME

(71) Applicant: Phong Duy Bui, San Diego, CA (US)

(72) Inventor: Phong Duy Bui, San Diego, CA (US)

(73) Assignee: Ikonx Incorporated, San Diego, CA (US)

( * ) Notice: Subject to any disclaimer, the term of this patent is extended or adjusted under 35 U.S.C. 154(b) by 0 days.

(21) Appl. No.: 16/899,731

(22) Filed: Jun. 12, 2020

Related U.S. Application Data

(60) Provisional application No. 63/008,692, filed on Apr. 11, 2020.

(51) Int. Cl.
| | | |
|---|---|---|
| A61M 16/00 | (2006.01) |
| A61M 16/08 | (2006.01) |
| A61M 16/06 | (2006.01) |
| A61M 16/04 | (2006.01) |

(Continued)

(52) U.S. Cl.
CPC .... *A61M 16/0087* (2013.01); *A61M 16/0463* (2013.01); *A61M 16/0672* (2014.02); *A61M 16/0891* (2014.02); *A61M 16/1005* (2014.02); *A61M 16/1055* (2013.01); *A61G 10/005* (2013.01); *A61M 2016/103* (2013.01); *A61M 2202/0208* (2013.01); *A61M 2202/0225* (2013.01); *A61M 2202/0241* (2013.01); *A61M 2202/203* (2013.01); *A61M 2202/206* (2013.01);

(Continued)

(58) Field of Classification Search
CPC ........... A61M 16/0087–0093; A61M 16/0672; A61M 16/0875–1005; A61M 16/0463; A61M 16/105–107; A61M 2016/102–1035; A61M 2202/0208; A61M 2202/0225; A61M 2202/0241; A61M 2202/203; A61M 2202/206; A61M 2205/053; A61M 2207/10; A61M 16/0488; A61G 10/00–04; A61G 1/013; A61B 90/40; A61B 2090/401; A62B 31/00
USPC ......................................................... 600/21
See application file for complete search history.

(56) References Cited

U.S. PATENT DOCUMENTS

| | | | | |
|---|---|---|---|---|
| 4,367,728 A | * | 1/1983 | Mutke ................. | A61G 10/005 128/205.26 |
| 4,787,894 A | * | 11/1988 | Turnbull ........... | A61M 16/0486 604/319 |
| 5,546,961 A | | 8/1996 | Harrison | |

(Continued)

OTHER PUBLICATIONS

"AIR Tent for Airway Management of SARS Patients", Canadian Journal of Anesthesiza, p. 854.

(Continued)

*Primary Examiner* — Kendra D Carter
*Assistant Examiner* — Elliot S Ruddie
(74) *Attorney, Agent, or Firm* — James R. McDaniel

(57) ABSTRACT

A patient airway dome including an adjustable frame having a hinge such that the hinge allows the frame to adjust between an erected position to create an airway dome and a collapsed position that allows the frame to lay flat, a dome covering located over the retractable frame, a plurality of ultraviolet lights operatively connected to the retractable frame, a plurality of superior glove access portals located on the dome covering, a plurality of inferior glove access portals located on the dome covering, an anesthesia circuit tube operatively connected to the dome covering, and an anesthesia machine connector operatively connected to the anesthesia circuit tube.

11 Claims, 5 Drawing Sheets

(51) Int. Cl.
*A61M 16/10* (2006.01)
*A61G 10/00* (2006.01)

(52) U.S. Cl.
CPC ... *A61M 2205/053* (2013.01); *A61M 2207/10* (2013.01)

(56) References Cited

U.S. PATENT DOCUMENTS

| | | | |
|---|---|---|---|
| 5,582,574 A * | 12/1996 | Cramer | A61G 10/026 128/205.26 |
| 5,865,182 A | 2/1999 | Chen | |
| 7,297,141 B2 | 11/2007 | Kathrani et al. | |
| 7,503,890 B2 | 3/2009 | Kubicsko et al. | |
| 8,697,000 B2 | 4/2014 | Reese et al. | |
| 8,739,797 B2 | 6/2014 | Bonutti | |
| 9,949,881 B2 | 4/2018 | Self et al. | |
| 10,016,252 B1 * | 7/2018 | Wren, Sr. | A61B 90/50 |
| 10,299,882 B2 | 5/2019 | Armout et al. | |
| 10,470,842 B2 | 11/2019 | Moore | |
| 2002/0045796 A1 * | 4/2002 | O'Connor | A61B 90/40 600/21 |
| 2003/0205230 A1 * | 11/2003 | Shusterman | A61H 31/02 128/205.26 |
| 2009/0093671 A1 * | 4/2009 | Maloney | A61G 10/005 600/21 |
| 2014/0316455 A1 * | 10/2014 | Gnanashanmugam | A61B 17/135 606/202 |
| 2016/0074268 A1 * | 3/2016 | Breegi | A61B 90/30 600/21 |

OTHER PUBLICATIONS

"Barrier tent provides medics against coronavirus exhaled by Covid-19 patients", Katarzyna Zachariasz, Podolokcovid-19, Technology, May 25, 2020.
"Emergency Relief Patient Cover", Copyright 2020, Stryker.

* cited by examiner

PATIENT AIRWAY DOME AND METHODS OF MAKING AND USING SAME

CROSS-REFERENCE TO RELATED APPLICATION

This application is a continuation-in-part of U.S. Patent Application 63/008,692, filed on Apr. 11, 2020, the disclosure of which is hereby incorporated by reference in its entirety to provide continuity of disclosure to the extent such a disclosure is not inconsistent with the disclosure herein.

FIELD OF THE INVENTION

The present invention is generally related to a patient airway dome. The patient airway dome is a novel, single-use, lightweight, disposable, collapsible, easy-to-use, secure, transparent covering extending around the patient's head and neck. It promotes safe bimanual airway intervention and resuscitation while protecting healthcare personnel from airborne pathogens. The airway dome provides a secure negative pressure protection around the patient to protect the healthcare worker. It provides optimal patient visualization with the ability for two pairs of hands to directly access the airway (to include bag-mask ventilation (BMV), high-flow nasal cannula (HFNC), laryngoscopy with intubation, cricoid pressure, airway suctioning, and bronchoscopy). The airway dome can be utilized for airway intervention in the intensive care unit (ICU), emergency department (ED), and operating room (OR), while also facilitating safe transport throughout the hospital for sick patients with airway intervention. It can also potentially be utilized away from the hospital in ambulances, hospice care, and nursing homes. The airway dome confines potentially dangerous airway secretions to a sealed area around the patients head and neck. This may safely allow multiple patients on ventilators to be cared for in smaller spaces or in large open makeshift hospitals in time of an epidemic. It may decrease the use of medical/surgical supplies which can be provided to other high-risk areas, decrease the cost of overall personal protective equipment (PPE), and provide lifesaving protection for healthcare workers involved in high risk airway procedures.

This new cost-effective patient PPE consists of transparent plastic sheeting, a collapsible frame, two pairs of access apertures with latex-free gloves, skin sensitive medical tape, a "push through" intubation bag, and portals for airway circuitry, videolaryngoscope, and suction.

BACKGROUND OF THE INVENTION

Prior to the present invention, as set forth in general terms above and more specifically below, it is known, that the SARS-CoV-2 virus is transmitted primarily by person-to-person contact through respiratory droplets and aerosols. This virus causes coronavirus disease 2019 (COVID-19), which may clinically present with flu-like symptoms (fever, cough, fatigue) and progress to acute respiratory failure (shortness of breath, pneumonia, acute respiratory distress).

Medical personnel caring for patients with respiratory failure from COVID-19 are at high risk of contracting the infection. Procedures generating aerosols such as bag-mask ventilation (BMV), high-flow nasal cannula (HFNC), and tracheal intubation (and extubation) are of particularly high risk.

Appropriate precautions are vital when providing these frequent respiratory services in the emergency department (ED), intensive care unit (ICU), and operating room (OR). Unfortunately, many hospitals lack personal protective equipment (PPE) of sufficiently high quality (n95 masks, powered air purifying respirators (PAPR), and negative pressure isolation) for urgent yet dangerous aerosol-generating procedures such as BMV, HFNC, intubation, and bronchoscopy.

With the COVID-19 pandemic, frequent life-saving upper airway intervention is critical yet very risky to the healthcare provider and staff. Over half of COVID-19 patients are afebrile early in the disease and can still spread SARS-CoV-2 with high efficiency. The virus is present in highest concentrations in the upper airway (nose and mouth) thereby placing those health care workers in primary and critical care, anesthesiology, otolaryngology, and dentistry at greatest risk. The latest figures reveal healthcare workers make up 9% of Italy's COVID-19 cases and 12% of cases in Spain. Not adequately protecting healthcare workers during an epidemic will cripple the healthcare system and exponentially increase patient morbidity and mortality. Healthcare workers are becoming infected at unprecedented rates. In fact, some hospital systems are now using a trash bag with a hole in it to attempt to minimize aerosolization during intubation.

It is a purpose of this invention to fulfill these and other needs in the patient airway dome art in a manner more apparent to the skilled artisan once given the following disclosure.

The preferred patient airway dome, according to various embodiments of the present invention, offers the following advantages: ease of use; lightness in weight; durability; reusability; the ability to easily see through the dome; foldability/collapsibility; the use of torsion springs to assist in keeping the dome taut for clear viewing; improved prevention of spreading a respiratory disease to the healthcare providers, first responders, and nearby surrounding people; the ability to allow two (2) or more patients with isolation precautions to be in the same room; portability; the ability to use the dome in a variety of medical and non-medical settings; the ability to be able to transport the dome with the patient from one area to another area; the use of multiple hand ports to allow medical personnel to perform medical procedures on the patient; the ability to use different size gloves while still maintaining an airtight seal; the ability to pre-oxygenate the dome; the ability to introduce a calming scent into the dome in order to ease the patients stress; the use of filters to prevent the release of bacteria and viruses through patient breathing; the use of filters to further minimize the spread of infection to the healthcare providers; the ability to provide multiple ports to connect to suction tubing for suctioning saliva, blood, or if the patient aspirates; the ability to provide suction ports having filters for creating a negative pressure in the dome in order to keep the respiratory disease inside of the dome; the use of a pass-through type sealable bag in order to transfer other needed instruments, medications, or other items needed that were not originally located under the dome prior to the beginning of the medical procedure; the ability to connect the dome to a vent and filter system that includes ultra-violet (UV) lighting inside the vent and filter system in order to eradicate or otherwise eliminate any viruses from circulating around the air after the air is exhausted out of the vent and filter system; the ability to provide filters within the vent and filter system to further prevent the leakage of any respiratory diseases; the ability to provide UV lights mounted within the dome to eradicate or otherwise eliminate any viruses expelled by the patient through breathing, coughing, gagging, sneezing, or any other disruption of the epithelial lining; and the ability of the UV lights in the dome to eradicate or otherwise eliminate any bacteria or viruses on the supplies and/or instruments located within the dome. In fact, in many of the preferred embodiments, these advantages are optimized to an extent that is considerably higher than heretofore achieved in prior, known patient airway domes.

BRIEF DESCRIPTION OF THE DRAWINGS

The above-mentioned features and steps of the invention and the manner of attaining them will become apparent, and the invention itself will be best understood by reference to the following description of the embodiments of the invention in conjunction with the accompanying drawings, wherein like characters represent like parts throughout the several views and in which.

DETAILED DESCRIPTION OF THE PREFERRED EMBODIMENTS OF THE INVENTION

In order to address the shortcomings of the prior, known patient airway domes, it would be desirable to utilize a single-use, collapsible, lightweight, disposable, easy-to-use, secure, transparent covering extending around the patient's head and neck. It promotes safe bimanual airway intervention and resuscitation while protecting healthcare personnel from airborne pathogens. The airway dome provides a secure negative pressure protection around the patient to protect the healthcare worker. It provides optimal patient visualization with the ability for two pairs of hands to directly access the airway (to include bag-mask ventilation (BMV), high-flow nasal cannula (HFNC), laryngoscopy with intubation, cricoid pressure, airway suctioning, and bronchoscopy).

Figure 1:
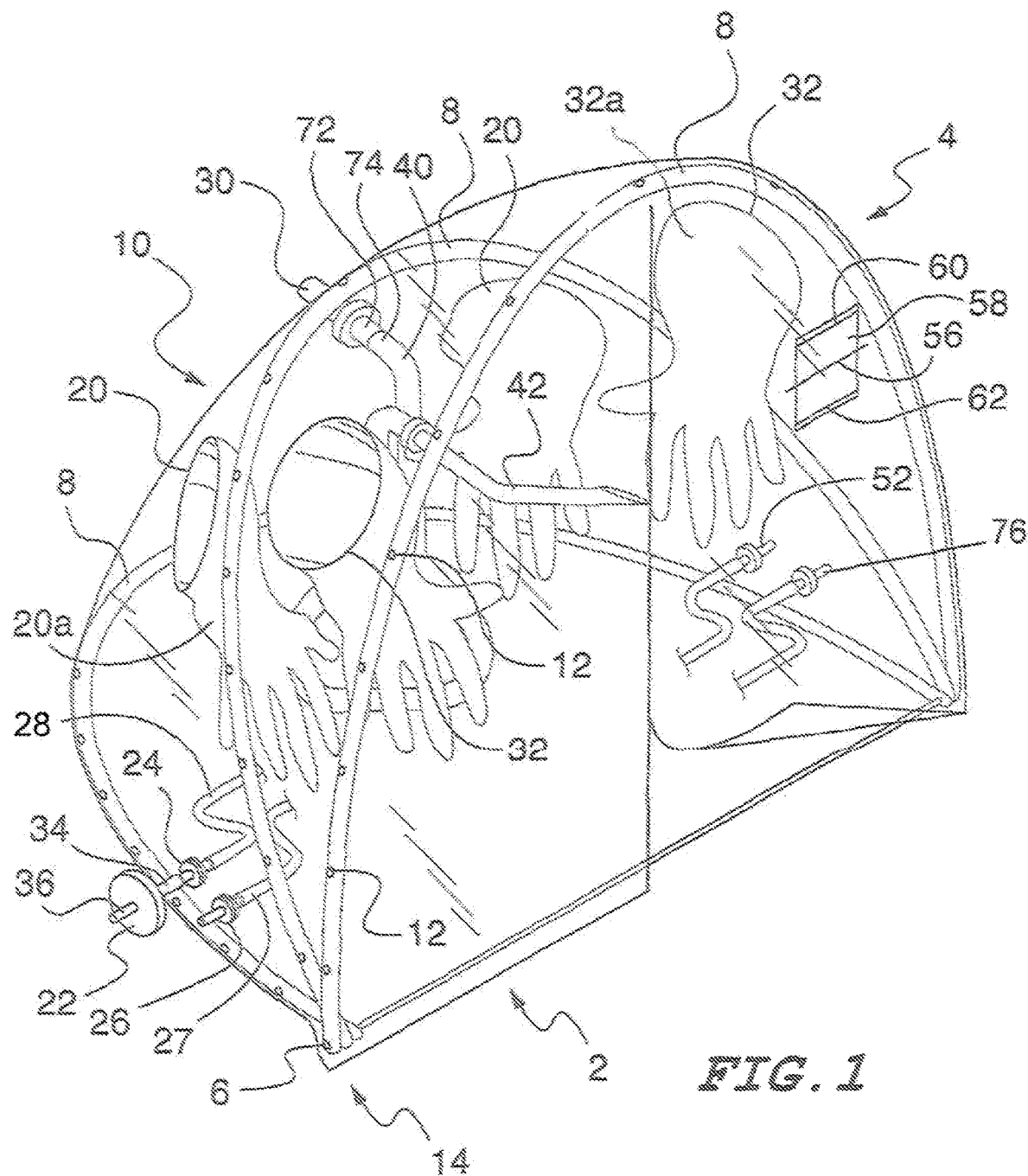
FIG. 1 is a schematic illustration of the patient airway dome in a fully unfolded position prior to a patient being introduced into the patient airway dome, constructed according the present invention.
Figure 2:
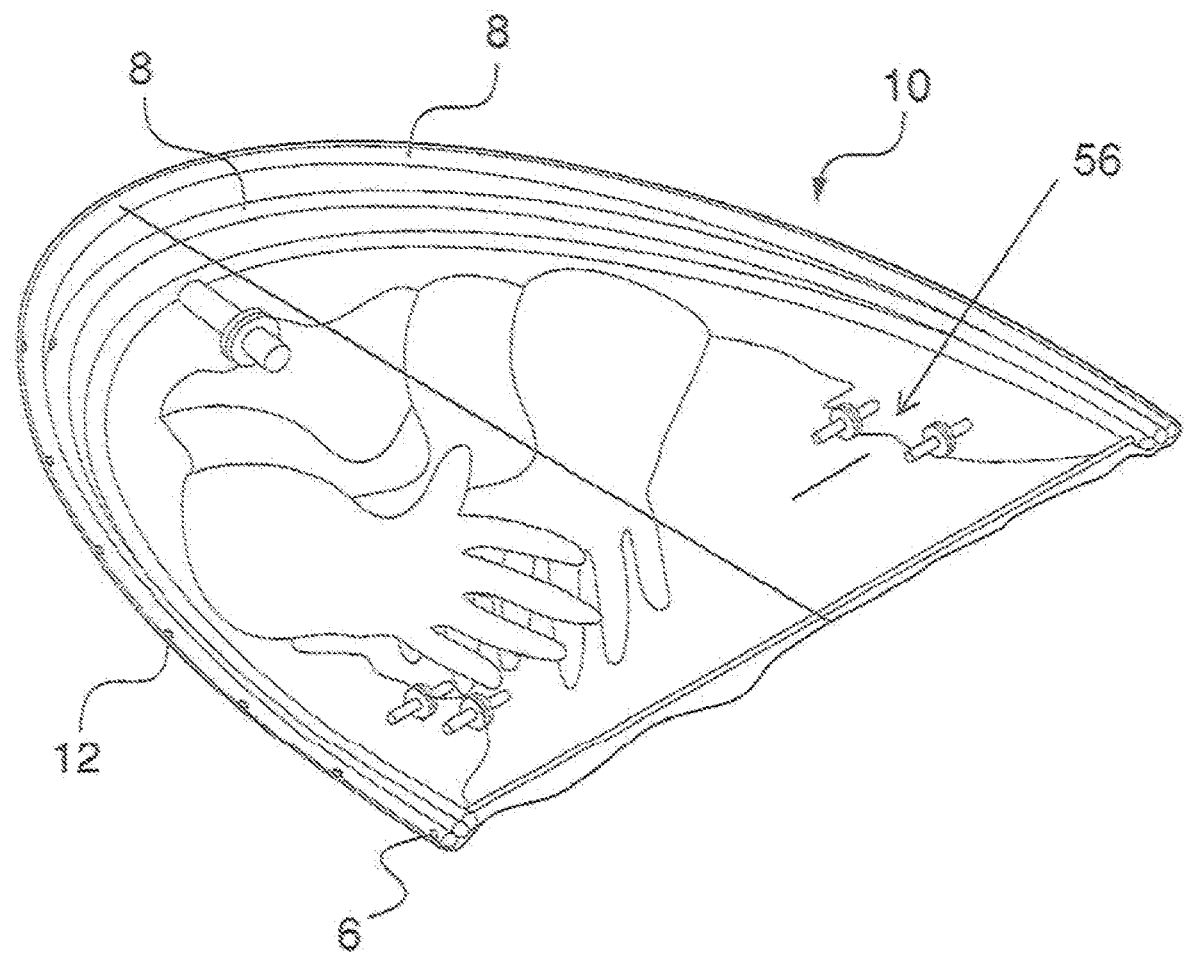
FIG. 2 is a schematic illustration of a patient airway dome in a folded or collapsed position, constructed according the present invention.
Figure 3:
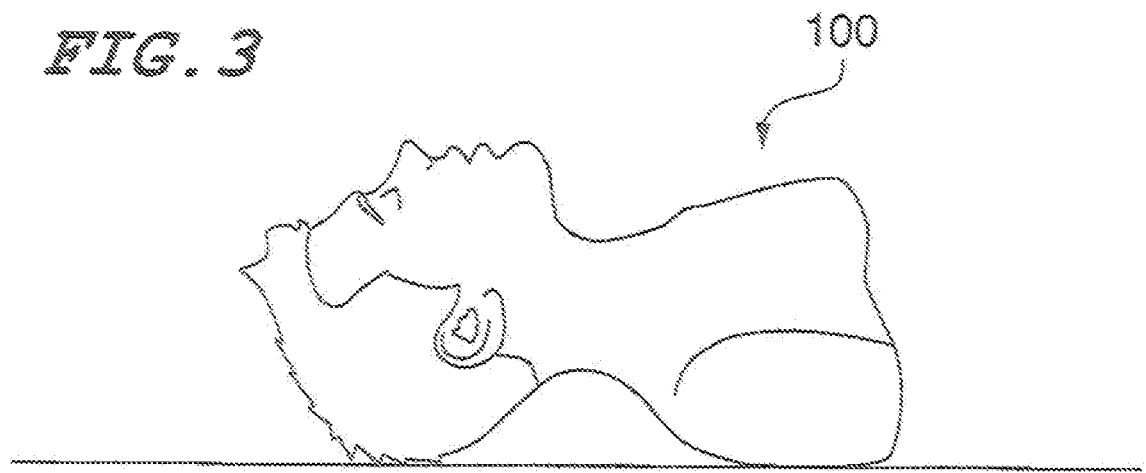
FIG. 3 is a schematic illustration of the patient.
Figure 4:
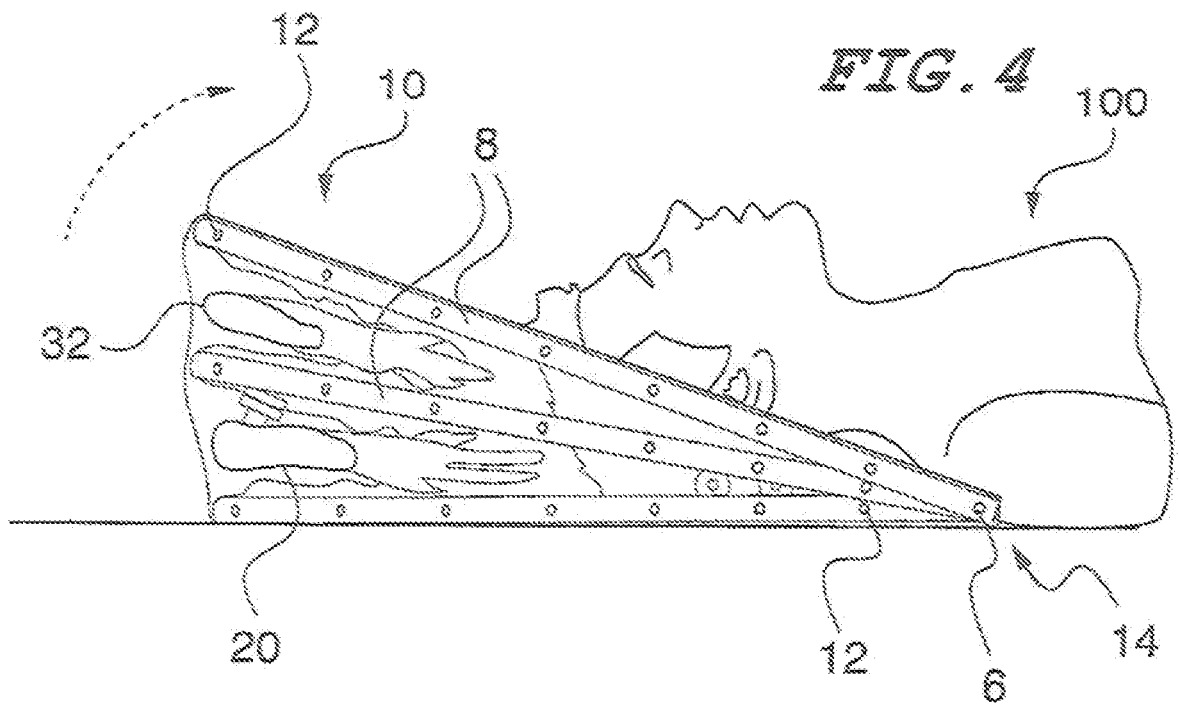
FIG. 4 is a schematic illustration of the patient airway dome in a semi-unfolded position with the patient being located within the dome, constructed according the present invention.
Figure 5:
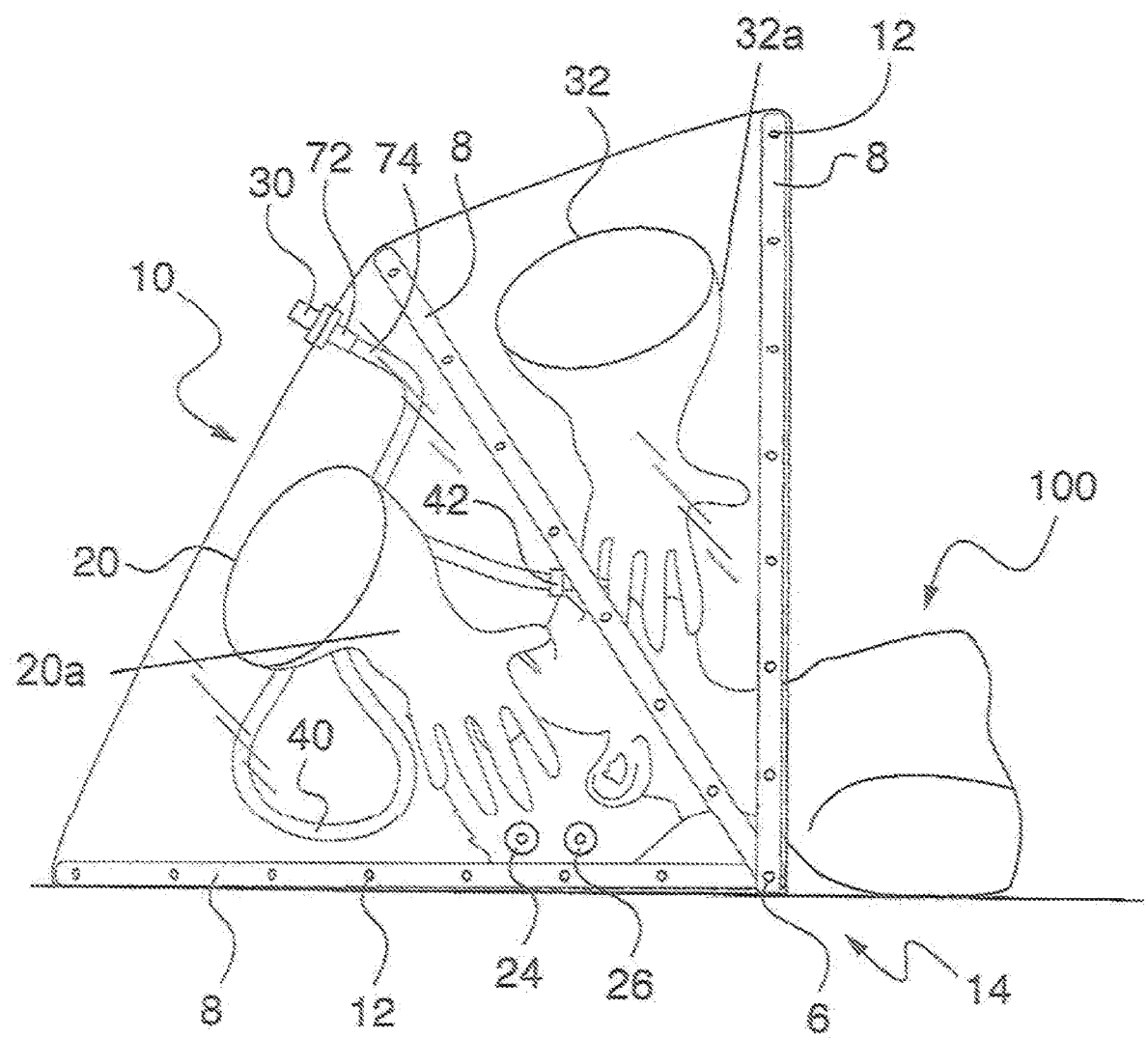
FIG. 5 is another schematic illustration of the patient airway dome in a fully unfolded position with the patient being located within the dome, constructed according the present invention.
Figure 6:
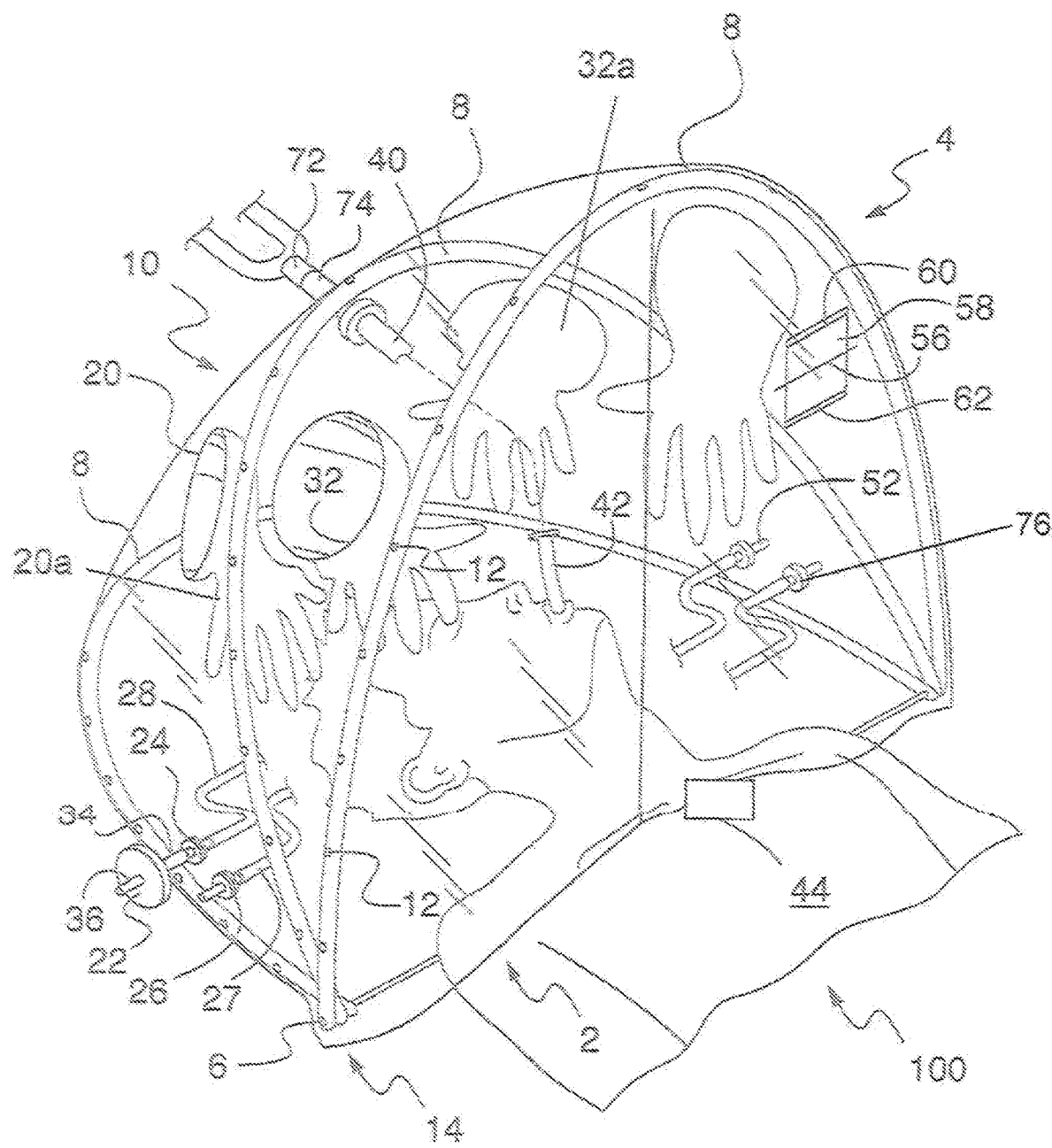
FIG. 6 is a schematic isometric illustration of the patient airway dome in a fully unfolded position with the patient being located within the dome, constructed according the present invention.

Reference is made now to FIGS. 1-5, where there is illustrated a patient airway dome (or patient isolation hood) 2, wherein the patient airway dome includes, in part, frame 4, hinge 6, frame legs 8, dome covering 10, and ultraviolet (UV) lights 12. Preferably, frame 4 (and frame legs 8), and hinge 6 are constructed of any suitable, durable, UV resistant, high strength, lightweight, and medical grade material. Also, dome covering 10 preferably, is constructed of any suitable, durable, UV resistant, high strength, lightweight, flexible, medical grade material, and transparent material. It is to be understood that dome covering 10 is conventionally attached to frame 4 by conventional fasteners (not shown). Furthermore, the construction of the patient airway dome 2 allows the patient airway dome 2 to be folded/collapsed (FIG. 2), partially erected (FIG. 4), and to be completely unfolded or erected (FIGS. 1, 5, and 6).

As shown in FIG. 1, frame 4 includes a plurality of frame legs 8 that are arcuate in shape. However, it is to be understood that frame legs 8 could also be rectangularly-shaped or square-shaped. The important consideration regarding the shape of frame legs 8 being that the shape of the frame legs 8 allows the patient airway dome 2 to be properly located over the patient, as will be described in greater detail later. Frame legs 8 are pivotally connected together by hinge 6. Finally, dome covering 10 is attached to frame legs 8 by UV lights 12.

Regarding FIG. 4, patient airway dome 2 is shown in a partially unfolded (partially erected) position. As shown in FIG. 4, the frame legs 8 are pulled apart from each other by the medical personnel which causes dome covering 10 to begin to stretch out. It is to be understood that torsion springs 14 are conventionally located within the frame legs 8 in order to help keep the patient airway dome 2 taut to provide for clear viewing of the patient's head and airway.

With respect to FIG. 5, patient airway dome 2 is shown in a completely unfolded (completely erected) position. As shown in FIG. 5, the frame legs 8 are now pulled even further apart from each other by the medical personnel which causes dome covering 10 to become almost completely stretched out. It is to be understood that in this fully erected position, torsion springs 14 will be utilized to help keep the patient airway dome 2 taut to provide for clear viewing of the patient's head and airway.

Regarding FIGS. 1, 5 and 6, it is to be understood that patient airway dome 2 can also be constructed to include superior glove access portals 20, viral filter 22, suction ports 24, 26, suction tubing 28, anesthesia machine connector 30, oxygen connection port 52 for a nasal cannula or an oxygen mask, slit 56, two-way opening (intubation) pouch 58 having pouch resealable openings 60 and 62, and patient 100. It is to be understood that superior glove access portals 20 are used by healthcare personnel superior to access the patient's head to manage the patient's airway and to intubate the patient 100. Furthermore, superior glove access portals 20 are conventionally connected to dome covering 10, preferably, on both side of patient airway dome 2. It is to be understood that each of the superior glove access portals 20 is attached to a conventional surgical glove 20a. Preferably, glove access portals 20 are constructed of any suitable, durable, UV resistant, high strength, lightweight, flexible, medical grade material. Finally, oxygen connection port 52 is, preferably, constructed of any suitable, durable, UV resistant, high strength, lightweight, medical grade material.

With respect to viral filter 22, viral filter 22 is used to minimize any viruses or bacteria from getting out of the patient airway dome 2. It is to be understood that viral filter 22 may be connected to all of the suction ports 24 and 26 or selected suction ports 24 and 26.

With respect to suction ports 24 and 26, suction ports 24 and 26 are conventionally located on both sides of patient airway dome 2. In this manner, port 26 accepts tubing for a conventional Yankauer tip suction (not shown) for suctioning saliva and blood from the patient 100. The other port 24 is conventionally connected to a conventional suction device (not shown) located external to the patient airway dome 2 to provide negative pressure inside the dome, as will discussed in greater detail later. It is to be understood that both ports 24 and 26 may connect a conventional "Y" joint 27 to the viral filter 22 and then suction tubing 28. It is to be understood that suction ports 24 and 26 can also include an open and close valve (not shown). In this manner, if the patient 100 needs to be transported, the connecting tubes to any of the suction ports 24 and 26 would have to be disconnected and closed by a valve so as to eliminate any virus for further escaping the patient airway dome 2.

Regarding suction tubing 28, suction tubing 28 is conventional suction tubing that is used to suction blood, saliva, or if the patient 100 aspirates. It is to be understood that anesthesia machine connector 30 is used to connect the anesthesia circuit tube 40 located with the patient airway dome 2 to a conventional anesthesia machine (not shown). Finally, patient 100 is shown as being located within patient airway dome 2.

Regarding FIGS. 1, 5 and 6, FIGS. 1, 5 and 6 illustrate that patient airway dome 2 also can include inferior glove access portals 32. It is to be understood that inferior glove access portals 32 are used by healthcare personnel inferior to access the patients head in order to assist healthcare personnel at the head of the patient's bed. Furthermore, inferior glove access portals 32 are conventionally connected to dome covering 10. It is to be understood that each of the inferior glove access portals 32 is attached to a conventional surgical glove 32a. Finally, superior glove access portal 20 is constructed of any suitable, durable, UV resistant, high strength, lightweight, flexible, medical grade material. It is to be understood that inferior glove access portals 32 should be located on both sides of patient airway dome 2. It is to be understood that each of the superior glove access portals 20 and inferior glove access portals 32 can include a window (not shown) that opens and closes when the medical personnel take his/her hand in and out of the surgical gloves and portals.

With respect to FIGS. 1, 5 and 6, FIGS. 1, 5 and 6 illustrate further details regarding viral filter 22. As shown in FIGS. 1, 5 and 6, viral filter 22 is connected to suction port 24 through the use of tube extension 34. The other side of viral filter 22 is connected to a suction device extension 36. It is to be understood that tube extension 34 and suction device extension 36, preferably, constructed of any suitable, durable, UV resistant, high strength, lightweight, flexible, medical grade material.

Regarding FIGS. 5 and 6, both superior glove access portals 20 and tubing 40 that connects to the endotracheal tube 42 located within the patient 100 are shown. As discussed earlier, superior glove access portals 20 are used by healthcare personnel superior to patient's head to manage airway and intubate the patient 100.

With respect to FIGS. 5 and 6, FIGS. 5 and 6 further show that tubing 40 is connected to the endotracheal tube 42 which has been located within the patient 100. Also, as shown in FIGS. 5 and 6, a portion of dome covering 10 is located over the chest area of the patient 100. A conventional medical grade adhesive tape 44 (FIG. 6) is used to conventionally secure the loose end of dome covering 10 onto the patient's chest. It is to be understood that patient airway dome 2 can also include a resealable "push-through" intubation pouch 58 having resealable openings 60 and 62 on its outside and inside, respectively, in order to allow movement of instruments and/or medications into and out of patient airway dome 2. It is to be understood that the intubation pouch 58 is retained with a slit 56 that is conventionally formed in patient airway dome 2. In this manner, if an instrument and/or medication that is needed for the medical procedure has not been placed within the patient airway dome 2 prior to the beginning of the medical procedure on the patient 100, the instrument and/or medication can be placed within the intubation bag 58 by opening the resealable opening 60, placing the instrument and/or medication into the intubation bag 58, resealing the resealable opening 60, opening the resealable opening 62 within the patient airway dome 2, removing the instrument and/or medication, and resealing the resealable opening 62.

With respect to FIGS. 1, 5 and 6, FIGS. 1, 5 and 6 provide another illustration of superior glove access portal 20 and tubing 40 that connects to the endotracheal tube 42 located within the patient 100. As can been seen in FIGS. 1, 5 and 6, dome covering 10 is constructed of a transparent material. As discussed earlier, dome covering 10 allows the healthcare provider to see the patient 100 and allow the patient 100 to see out of the patient airway dome 2 in case the patient is feeling claustrophobic.

Regarding FIGS. 1, 5, and 6, FIGS. 1, 5, and 6 provide illustrations of inferior glove access portals 32 and tubing 40 that connects to the endotracheal tube 42 located within the patient 100. As discussed earlier, inferior glove access portals 32 are used by healthcare personnel inferior to the patient's head to assist healthcare personnel at head of bed.

Regarding FIGS. 1, 5, and 6, FIGS. 1, 5, and 6 illustrate another embodiment of viral filter 22 and suction tubing 50. As shown in FIGS. 1, 5, and 6, viral filter 22 is connected to suction port 24 through the use of tube extension 34. The other side of viral filter 22 is connected to a suction device extension 36. However, in this embodiment suction port 26 is connected to a conventional vacuum device (not shown) which provides negative pressure to patient airway dome 2.

A unique aspect of the present invention is the use of a conventional vacuum device (not shown) which provides negative pressure to patient airway dome 2. The use of the negative pressure within the patient airway dome 2 creates negative pressure in the patient airway dome 2 to keep any the respiratory diseases from the patient 100 inside the patient airway dome 2, thereby minimizing any particles from leaking out of the patient airway dome 2.

With respect to FIGS. 1, 5, and 6, FIGS. 1, 5, and 6 illustrate conventional anesthesia machine tubing (not shown) being connected to tubing 40 that connects to the endotracheal tube 42 located within the patient 100. The anesthesia machine can be used to conventionally provide conventional anesthesia to the patient 100 while the patient 100 is located within the patient airway dome 2. It is to be further understood that an end-tidal carbon dioxide monitor connector 72 can be located between anesthesia machine tubing and tubing 40 such that end-tidal carbon dioxide monitor connector 72 can be conventionally used to confirm proper endotracheal placement in the trachea of the patient 100. Also, a viral filter 74 is conventionally located between anesthesia machine tubing and tubing 40. This viral filter 74 provides another filter outside of the patient airway dome 2 that is connected to the suction device (not shown). It is to be further understood that a second end-tidal carbon dioxide monitor connector 76 can be located adjacent to oxygen connection port 52 (FIGS. 1 and 6).

Another unique aspect of the present invention is that the patient airway dome 2 allows for two (2) or more patients with isolation precautions to be in the same room, as it minimizes the risk of airway disease infections. It is to be understood that the patient airway dome 2 could also be used in a large auditorium or makeshift tent. In this manner, the patient airway dome 2 may allow hundreds or thousands of patients to be in the same large room, as their breathing isolation is kept to themselves.

A still another unique aspect of the present invention is that the patient airway dome 2 is lightweight, portable, and can be easily carried and then used in many areas including emergency rooms, intensive care units (ICU), surgery, medical/surgical floor, transportation within the hospital, ambulance, accident scenes, prison and jail medical wards, hospice care, nursing homes, patient homes, and any other possible airway disease related areas. Furthermore, the patient airway dome 2 can stay with the patient 100 from one department to the next or from the medical ward to another ward. This helps minimize the risk during transportation.

A yet another unique aspect of the present invention is that a calming scent (not shown) can be infused into the patient airway dome 2 during pre-oxygenation as well to help ease the patient's stress.

A still another unique aspect of the present invention is that the ventilation and filter system can be equipped with ultraviolet (UV) lighting (not shown) inside the ventilation box (not shown) which will eradicate or otherwise eliminate any viruses from circulating around the air after the air is exhausted out of the vent and filter system. This greatly decreases the airborne disease from escaping into the procedure area if any did escape at all.

Finally, another unique aspect of the present invention is that the patient airway dome 2 can be equipped with UV lights 12 conventionally mounted on the inside of the patient airway dome 2 in order to eradicate or otherwise eliminate any the bacteria or viruses expelled by the patient though breathing, coughing, gagging, sneezing or disruption of the patient's epithelial lining which are where most respiratory diseases are at but not limited to. Furthermore, the UV lights 12 located on the inside of the patient airway dome 2 can also be used to eradicate or otherwise eliminate any bacteria and viruses that may be located on the supplies and/or instruments located within the patient airway dome 2. It is to be understood that the UV lights 12 may be of a single light spectrum or a broad spectrum and can be continuous lighting or a high pulse lighting.

Operation of the Patient Airway Dome

With respect to the operation of the patient airway dome 2 and with reference to FIGS. 1-6, assume that an adult male (patient 100 as shown in FIG. 3) arrives in the emergency department (ED) with suspected COVID-19 and a progressive acute airway distress requiring urgent intubation. Routine principles of airway management are followed to include personal protective equipment (PPE) such as mask, gloves, eye protection, and gown. It is to be understood that medical treatment consent of the patient 100 should be obtained, when possible.

The airway specialist then procures the appropriate standard equipment for intubation and places them in the resealable plastic intubation "push through" bag 58 to place inside the patient airway dome 2. It is to be understood that the equipment may include an appropriate endotracheal tube or a laryngeal mask airway (LMA) with one size smaller, a tube securement device, a syringe to inflate the tube cuff, an inline suction, a videolaryngoscope (CMAC or Glidescope), a nasogastric tube, and/or a non-vented mask.

The patient 100 is placed in a supine position with a conventional chux pad (not shown) conventionally located underneath the patient 100. The patient airway dome 2 is opened and positioned over the patient's head and neck to the upper thorax (FIG. 4), as described above.

Skin sensitive medical tape 44 (FIG. 6) is placed along the inferior edges of the dome to seal the dome to the neck, torso and underlying chux pad.

A viral filter 22 is placed on the outside dome suction port 24 and linked to a conventional suction device (not shown) to provide negative pressure.

Using the superior glove access portals 20, the inflated mask (not shown) is placed over the nose and mouth of the patient 100 for pre-oxygenation. The mask is connected to anesthesia machine connector 30. A second viral filter 74 is placed on the outside of patient airway dome 2 followed by the anesthesia airway ventilator tubing (not shown).

An end-tidal CO2 monitor connector 72 may be placed between the ventilator tubing (not shown) and viral filter 74. All connections are conventionally secured such as by adhesive tape or the like. Also, another end-tidal CO2 monitor connector 76 can be located adjacent to oxygen connection port 52.

It is to be understood that rapid sequence anesthesia induction is recommended. Medical paralysis of the patient 100 is done prior to intubation with the endotracheal tube 42 to avoid coughing and subsequent aerosolization of particles by the patient 100.

The patient 100 is intubated with a videolaryngoscope (not shown) (or regular laryngoscope, if desired) through the superior glove access portals 20 and surgical gloves 20a utilizing an assistant through the inferior glove access portals 32 and surgical gloves 32a for cricoid pressure by removing tube stylet (not shown), inflating the tube cuff (not shown), securing with tape 44, and conventional in-line suction, as needed.

The placement of the endotracheal in the trachea of the patient 100 is ensured by conventional capnography through the use of end-tidal CO2 monitor connectors 72 and 76. In this manner, connectors 72 and 76 can be utilized to ensure the endotracheal placement in the trachea of the patient 100 is correct and then continue ventilating.

After the medical procedure has been completed on the patient 100, the patient 100 is transferred to a conventional hospital bed (not shown) for transport to the intensive care unit (ICU) with ventilation via bag-mask ventilation (BMV). A unique aspect of the present invention is that the ventilation bag is located outside the patient airway dome 2. Once in the ICU, any patient tubing located outside of the patient airway dome 2 may be conventionally connected to a ventilator (not shown). It is to be further understood that planned extubation will occur with the patient airway dome 2 in place which reduces the likelihood that any bacteria and viruses that may be possibly expelled by the patient through breathing, coughing, gagging, sneezing, or any other disruption of the epithelial lining will be contained within the patient airway dome 2. Finally, the patient airway dome 2 is conventionally disposed of when no longer needed.

The preceding merely illustrates the principles of the invention. It will thus be appreciated that those skilled in the art will be able to devise various arrangements which, although not explicitly described or shown herein, embody the principles of the invention and are included within its spirit and scope. Furthermore, all examples and conditional language recited herein are principally intended expressly to be only for pedagogical purposes and to aid the reader in understanding the principles of the invention and the concepts contributed by the inventors to furthering the art and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents and equivalents developed in the future, i.e., any elements developed that perform the same function, regardless of structure.

This description of the exemplary embodiments is intended to be read in connection with the figures of the accompanying drawing, which are to be considered part of the entire written description. In the description, relative terms such as "lower," "upper," "horizontal," "vertical," "above," "below," "up," "down," "top" and "bottom" as well as derivatives thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety.

The applicant reserves the right to physically incorporate into this specification any and all materials and information from any such patents, publications, scientific articles, web sites, electronically available information, and other referenced materials or documents to the extent such incorporated materials and information are not inconsistent with the description herein.

All of the features disclosed in this specification may be combined in any combination. Thus, unless expressly stated otherwise, each feature disclosed is only an example of a generic series of equivalent or similar features.

The specific methods and compositions described herein are representative of preferred embodiments and are exemplary and not intended as limitations on the scope of the invention. Other objects, aspects, and embodiments will occur to those skilled in the art upon consideration of this specification and are encompassed within the spirit of the invention. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, the terms "comprising", "including", "containing", etc. are to be read expansively and without limitation. The methods and processes illustratively described herein suitably may be practiced in differing orders of steps, and that they are not necessarily restricted to the orders of steps indicated herein.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention. Thus, it will be understood that although the present invention has been specifically disclosed by various embodiments and/or preferred embodiments and optional features, any and all modifications and variations of the concepts herein disclosed that may be resorted to by those skilled in the art are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein.

Other modifications and implementations will occur to those skilled in the art without departing from the spirit and the scope of the invention. Accordingly, the description hereinabove is not intended to limit the invention.

Therefore, provided herein is a new and improved patient airway dome, which according to various embodiments of the present invention, offers the following advantages: ease of use; lightness in weight; durability; reusability; the ability to easily see through the dome; foldability/collapsibility; the use of torsion springs to assist in keeping the dome taut for clear viewing; improved prevention of spreading a respiratory disease to the healthcare providers, first responders, and nearby surrounding people; the ability to allow two (2) or more patients with isolation precautions to be in the same room; portability; the ability to use the dome in a variety of medical and non-medical settings; the ability to be able to transport the dome with the patient from one area to another area; the use of multiple hand ports to allow medical personnel to perform medical procedures on the patient; the ability to use different size gloves while still maintaining an airtight seal; the ability to pre-oxygenate the dome; the ability to introduce a calming scent into the dome in order to ease the patient's stress; the use of filters to prevent the release of bacteria and viruses through patient breathing; the use of filters to further minimize the spread of infection to the healthcare providers; the ability to provide multiple ports to connect to suction tubing for suctioning saliva, blood, or if the patient aspirates; the ability to provide suction ports having filters for creating a negative pressure in the dome in order to keep the respiratory disease inside of the dome; the use of a pass-through type sealable bag in order to transfer other needed instruments, medications, or other items needed that were not originally located under the dome prior to the beginning of the medical procedure; the ability to connect the dome to a vent and filter system that includes ultra-violet (UV) lighting inside the vent and filter system in order to eradicate or otherwise eliminate any viruses from circulating around the air after the air is exhausted out of the vent and filter system; the ability to provide filters within the vent and filter system to further prevent the leakage of any respiratory diseases; the ability to provide UV lights mounted within the dome to eradicate or otherwise eliminate any viruses expelled by the patient through breathing, coughing, gagging, sneezing, or any other disruption of the epithelial lining; and the ability of the UV lights in the dome to eradicate or otherwise eliminate any bacteria or viruses on the supplies and/or instruments located within the dome.

In fact, in many of the preferred embodiments, these advantages of ease of use, lightness in weight, durability, reusability, the ability to easily see through the dome; foldability/collapsibility, the use of torsion springs to assist in keeping the dome taut for clear viewing; improved prevention of spreading a respiratory disease to the healthcare providers, first responders, and nearby surrounding people, the ability to allow two (2) or more patients with isolation precautions to be in the same room, portability, the ability to use the dome in a variety of medical and non-medical settings, the ability to be able to transport the dome with the patient from one area to another area, the use of multiple hand ports to allow medical personnel to perform medical procedures on the patient, the ability to use different size gloves while still maintaining an airtight seal, the ability to pre-oxygenate the dome, the ability to introduce a calming scent into the dome in order to ease the patient's stress, the use of filters to prevent the release of bacteria and viruses through patient breathing, the use of filters to further minimize the spread of infection to the healthcare providers, the ability to provide multiple ports to connect to suction tubing for suctioning saliva, blood, or if the patient aspirates, the ability to provide suction ports having filters for creating a negative pressure in the dome in order to keep the respiratory disease inside of the dome, the use of a pass-through type sealable bag in order to transfer other needed instruments, medications, or other items needed that were not originally located under the dome prior to the beginning of the medical procedure, the ability to connect the dome to a vent and filter system that includes ultra-violet (UV) lighting inside the vent and filter system in order to eradicate or otherwise eliminate any viruses from circulating around the air after the air is exhausted out of the vent and filter system, the ability to provide filters within the vent and filter system to further prevent the leakage of any respiratory diseases, the ability to provide UV lights mounted within the dome to eradicate or otherwise eliminate any viruses expelled by the patient through breathing, coughing, gagging, sneezing, or any other disruption of the epithelial lining, and the ability of the UV lights in the dome to eradicate or otherwise eliminate any bacteria or viruses on the supplies and/or instruments located within the dome are optimized to an extent that is considerably higher than heretofore achieved in prior, known patient airway domes.

I claim:

1. A patient airway dome for covering a patient's head and shoulders, comprising: an adjustable frame having at least three frame legs and two hinges, wherein the two hinges are located a predetermined distance from each other such that each hinge is rotatably connected to an end of each of the frame legs in order to allow the frame to adjust between an erected position to create an airway dome for covering a patient's head and shoulders and a collapsed position that allows the frame to lay flat;
a dome covering attached to the adjustable frame in the erected and collapsed positions, wherein the adjustable frame is located inside of the dome covering, wherein the dome covering creates the airway dome when the adjustable frame is in the erected position; such that, when the adjustable frame is in the erected position, the dome covering isolates the head and shoulders of the patient from a rest of the patient;
a plurality of individual ultraviolet lights located along each of the frame legs of the adjustable frame;
a plurality of suction ports connected to the dome covering and connected to a suction device located external to the airway dome to provide negative pressure inside the airway dome to keep any patient respiratory diseases inside the airway dome, thereby minimizing any particles from leaking out of the airway dome;
a plurality of superior glove access portals located on the dome covering; a plurality of inferior glove access portals located on the dome covering and located adjacent to the plurality of superior glove access portals; an anesthesia circuit tube operatively connected to the dome covering, wherein the anesthesia circuit tube is located within the airway dome when the frame is in the erected position; and an anesthesia machine connector operatively connected to the anesthesia circuit tube, wherein the anesthesia machine connector is located outside of the airway dome when the frame is in the erected position.

2. The patient airway dome, according to claim 1, wherein the patient airway dome is further comprised of:
a plurality of superior gloves such that each of the plurality of superior gloves is operatively connected to each of the plurality of superior glove access portals; and
a plurality of inferior gloves such that each of the plurality of inferior gloves is operatively connected to each of the plurality of inferior glove access portals.

3. The patient airway dome, according to claim 1, wherein the patient airway dome is further comprised of:
a first viral filter operatively connected to one of the plurality of suction ports.

4. The patient airway dome, according to claim 1, wherein the patient airway dome is further comprised of:
a second viral filter connected to the anesthesia circuit tube; and
an end-tidal carbon dioxide monitor connector connected to the second viral filer and the anesthesia machine connector, wherein the end-tidal carbon dioxide monitor connector is configured to be connected to a carbon dioxide monitor.

5. The patient airway dome, according to claim 1, wherein the patient airway dome is further comprised of:
an oxygen connection port operatively connected to the dome covering.

6. The patient airway dome, according to claim 1, wherein the patient airway dome is further comprised of:
a slit located on a portion of the dome covering; and
a resealable intubation pouch having a plurality of resealable openings, wherein the resealable intubation pouch is retained in the slit.

7. A method of constructing a patient airway dome for covering a patient's head and shoulders, comprising:
providing an adjustable frame having at least three frame legs and two hinges, wherein the two hinges are located a predetermined distance from each other, such that each hinge is rotatably connected to an end of each of the frame legs in order to allow the frame to adjust between an erected position to create an airway dome for covering a patient's head and shoulders and a collapsed position that allows the frame to lay flat;
attaching a dome covering over the adjustable frame such that the dome covering is located over the adjustable frame in the erected and collapsed positions, wherein the dome covering creates the airway dome when the adjustable frame is in the erected position such that, when the adjustable frame is in the erected position, the dome covering isolates the head and shoulders of the patient from a rest of the patient;
attaching a plurality of individual ultraviolet lights along each of the frame legs of the adjustable frame;
attaching a plurality of suction ports to the dome covering, wherein each of the plurality of suction ports is connected to a suction device located external to the airway dome to provide negative pressure inside the airway dome to keep any patient respiratory diseases inside the airway dome, thereby minimizing any particles from leaking out of the airway dome;
creating a plurality of superior glove access portals on the dome covering;

creating a plurality of inferior glove access portals on the dome covering such that the plurality of inferior glove access portals is located adjacent to the plurality of superior glove access portals;

attaching an anesthesia circuit tube to the dome covering, wherein the anesthesia circuit tube is located within the airway dome when the frame is in the erected position; and attaching an anesthesia machine connector to the anesthesia circuit tube, wherein the anesthesia machine connector is located outside of the airway dome when the frame is in the erected position.

8. The method of constructing the patient airway dome, according to claim 7, wherein the method is further comprised of:

attaching a plurality of superior gloves to the plurality of superior glove access portals such that each of the plurality of superior gloves is operatively connected to each of the plurality of superior glove access portals; and attaching a plurality of inferior gloves to the plurality of inferior glove access portals such that each of the plurality of inferior gloves is operatively connected to each of the plurality of inferior glove access portals.

9. The method of constructing the patient airway dome, according to claim 7, wherein the method is further comprised of:

attaching a first viral filter to one of the plurality of suction ports.

10. The method of constructing the patient airway dome, according to claim 7, wherein the method is further comprised of:

attaching a second viral filter to the anesthesia circuit tube; and attaching an end-tidal carbon dioxide monitor connector to the second viral filter and the anesthesia machine connector, wherein the end-tidal carbon dioxide monitor connector is configured to be connected to a carbon dioxide monitor.

11. The method of constructing the patient airway dome, according to claim 7, wherein the method is further comprised of:

creating a slit on a portion of the dome covering; and attaching a resealable intubation pouch having a plurality of resealable openings on a portion of the dome covering, wherein the resealable intubation pouch is retained in the slit.

* * * * *